United States Patent [19]

Roby et al.

[11] Patent Number: 5,403,347
[45] Date of Patent: Apr. 4, 1995

[54] ABSORBABLE BLOCK COPOLYMERS AND SURGICAL ARTICLES FABRICATED THEREFROM

[75] Inventors: Mark S. Roby, Killingworth; Steven L. Bennett, New Haven; Cheng-Kung Liu, Norwalk, all of Conn.

[73] Assignee: United States Surgical Corporation, Norwalk, Conn.

[21] Appl. No.: 204,721

[22] Filed: Mar. 2, 1994

Related U.S. Application Data

[63] Continuation-in-part of Ser. No. 68,811, May 27, 1993, abandoned.

[51] Int. Cl.$^6$ .................. C08G 64/18; C08G 64/02; C08G 63/06; C08G 63/08
[52] U.S. Cl. .................. 606/230; 606/77; 606/151; 606/219; 525/411; 525/413; 525/415; 528/354
[58] Field of Search ............ 525/411, 413, 415; 528/354; 606/77, 151, 219, 230

[56] References Cited

U.S. PATENT DOCUMENTS

| | | |
|---|---|---|
| 2,668,162 | 2/1954 | Lowe . |
| 2,683,136 | 7/1954 | Higgins . |
| 2,703,316 | 3/1955 | Schneider . |
| 2,758,987 | 8/1956 | Salzberg . |
| 3,225,766 | 12/1965 | Baptisti et al. . |
| 3,268,486 | 8/1966 | Klootwijk . |
| 3,268,487 | 8/1966 | Klootwijk . |
| 3,297,033 | 1/1967 | Schmitt . |
| 3,422,181 | 1/1969 | Chirgwin, Jr. . |
| 3,442,871 | 5/1969 | Schmitt et al. . |
| 3,463,158 | 8/1969 | Schmitt et al. . |
| 3,468,853 | 9/1969 | Schmitt et al. . |
| 3,531,561 | 9/1970 | Trehu . |
| 3,565,869 | 2/1971 | DeProspero . |
| 3,597,449 | 8/1971 | DeProspero et al. . |
| 3,620,218 | 11/1971 | Schmitt et al. . |
| 3,626,948 | 12/1971 | Glick et al. . |
| 3,636,956 | 1/1972 | Schneider . |
| 3,733,919 | 5/1973 | Kupp, II .................. 74/242.16 |
| 3,736,646 | 6/1973 | Schmitt et al. .................. 29/458 |
| 3,739,773 | 6/1973 | Schmitt et al. .................. 128/92 R |
| 3,772,420 | 11/1973 | Glick et al. . |
| 3,781,349 | 12/1973 | Ramsey et al. . |
| 3,784,585 | 1/1974 | Schmitt et al. . |
| 3,792,010 | 2/1974 | Wasserman et al. . |
| 3,797,499 | 3/1974 | Schneider .................. 128/334 R |
| 3,839,297 | 10/1974 | Wasserman et al. .................. 128/335.5 |
| 3,846,382 | 11/1974 | Ramsey et al. . |
| 3,867,190 | 2/1975 | Schmitt et al. .................. 128/335.5 |
| 3,878,284 | 4/1975 | Schmitt et al. .................. 264/184 |
| 3,896,802 | 7/1975 | Williams .................. 128/149 |
| 3,902,497 | 9/1975 | Casey .................. 128/296 |
| 3,937,223 | 2/1976 | Roth .................. 128/325 |
| 3,982,543 | 9/1976 | Schmitt et al. .................. 128/335.5 |

(List continued on next page.)

FOREIGN PATENT DOCUMENTS

| | | |
|---|---|---|
| 779291 | 7/1957 | United Kingdom . |
| 1332505 | 10/1973 | United Kingdom . |
| 1414600 | 11/1975 | United Kingdom . |
| 2102827 | 2/1983 | United Kingdom . |

OTHER PUBLICATIONS

D. K. Gilding. et al., "Biodegradable Polymers for Use in Surgery–Polyglycolic/poly(lache acid) Homo–and Copolymers: 1" Polymer, vol. 20, pp. 1459–1464 (1979).

D. F. Williams (ed.) Biocompatibility of Clinical Implant Materials, vol. II, Chapter 9: "Biodegradable Polymers" (1981).

*Primary Examiner*—David Buttner

[57] ABSTRACT

Block copolymers wherein one of the blocks is made from hard phase forming monomers and another of the blocks is made from soft phase forming monomers copolymerized with randomly intermingled units of other soft phase forming monomers. The copolymers are useful in forming surgical articles, including both monofilament and multifilament sutures. The block copolymer preferably comprising:

a) a proportion of glycolic acid ester units as end blocks, and
b) a center block comprising 1,4 dioxan-2-one randomly polymerized with 1,3 dioxane-2-one.

17 Claims, 1 Drawing Sheet

U.S. PATENT DOCUMENTS

| | | | |
|---|---|---|---|
| 3,987,937 | 10/1976 | Coucher | 222/193 |
| 4,033,938 | 7/1977 | Augurt et al. | |
| 4,045,418 | 8/1977 | Sinclair . | |
| 4,052,988 | 10/1977 | Doddi et al. | 128/335.5 |
| 4,057,537 | 11/1977 | Sinclair . | |
| 4,060,089 | 11/1977 | Noiles | 128/325 |
| 4,137,921 | 2/1979 | Okuzumi et al. | 128/335.5 |
| 4,157,437 | 6/1979 | Okuzumi et al. | 528/354 |
| 4,243,775 | 1/1981 | Rosensaft et al. | 525/415 |
| 4,246,904 | 1/1981 | Kaplan | 525/444 |
| 4,273,920 | 6/1981 | Nevin | 528/361 |
| 4,275,813 | 6/1981 | Noiles | 206/339 |
| 4,279,249 | 7/1981 | Vert et al. | 525/415 |
| 4,300,565 | 11/1981 | Rosensaft et al. | 528/354 |
| 4,429,080 | 1/1984 | Casey et al. | 525/415 |
| 4,643,191 | 2/1987 | Bezwada et al. | 525/415 |
| 4,653,497 | 3/1987 | Bezwada et al. | 525/415 |
| 4,705,820 | 11/1987 | Wang et al. | 524/381 |
| 4,744,365 | 5/1988 | Kaplan et al. | 528/354 |
| 4,788,979 | 12/1988 | Jarrett et al. | 528/354 |
| 4,791,929 | 12/1988 | Jarrett et al. | 528/354 |
| 4,838,267 | 6/1989 | Jamiolkowski et al. | 525/415 |
| 4,891,263 | 1/1990 | Kotliar et al. | 528/370 |
| 4,916,193 | 4/1990 | Tang et al. | 525/413 |
| 4,916,207 | 4/1990 | Boyle, Jr. et al. | 528/370 |
| 4,920,203 | 4/1990 | Tang et al. | 525/409 |
| 5,007,923 | 4/1991 | Bezwada et al. | 525/411 |
| 5,037,950 | 8/1991 | Bezwada et al. | 528/354 |
| 5,066,772 | 11/1991 | Tang et al. | 528/354 |
| 5,080,665 | 1/1992 | Jarrett et al. | 528/354 |
| 5,120,802 | 6/1992 | Mares et al. | 525/415 |
| 5,133,739 | 7/1992 | Bezwada et al. | 528/357 |
| 5,145,945 | 9/1992 | Tang et al. | 528/370 |
| 5,152,781 | 10/1992 | Tang et al. | 606/230 |
| 5,185,408 | 2/1993 | Tang et al. | 525/415 |
| 5,225,520 | 7/1993 | Kennedy et al. | 528/354 |
| 5,236,444 | 8/1993 | Muth et al. | 525/411 |
| 5,252,701 | 10/1993 | Jarrett et al. | 528/354 |
| 5,314,989 | 5/1994 | Kennedy et al. | 525/415 |
| 5,322,925 | 6/1994 | Muth et al. | 525/415 |

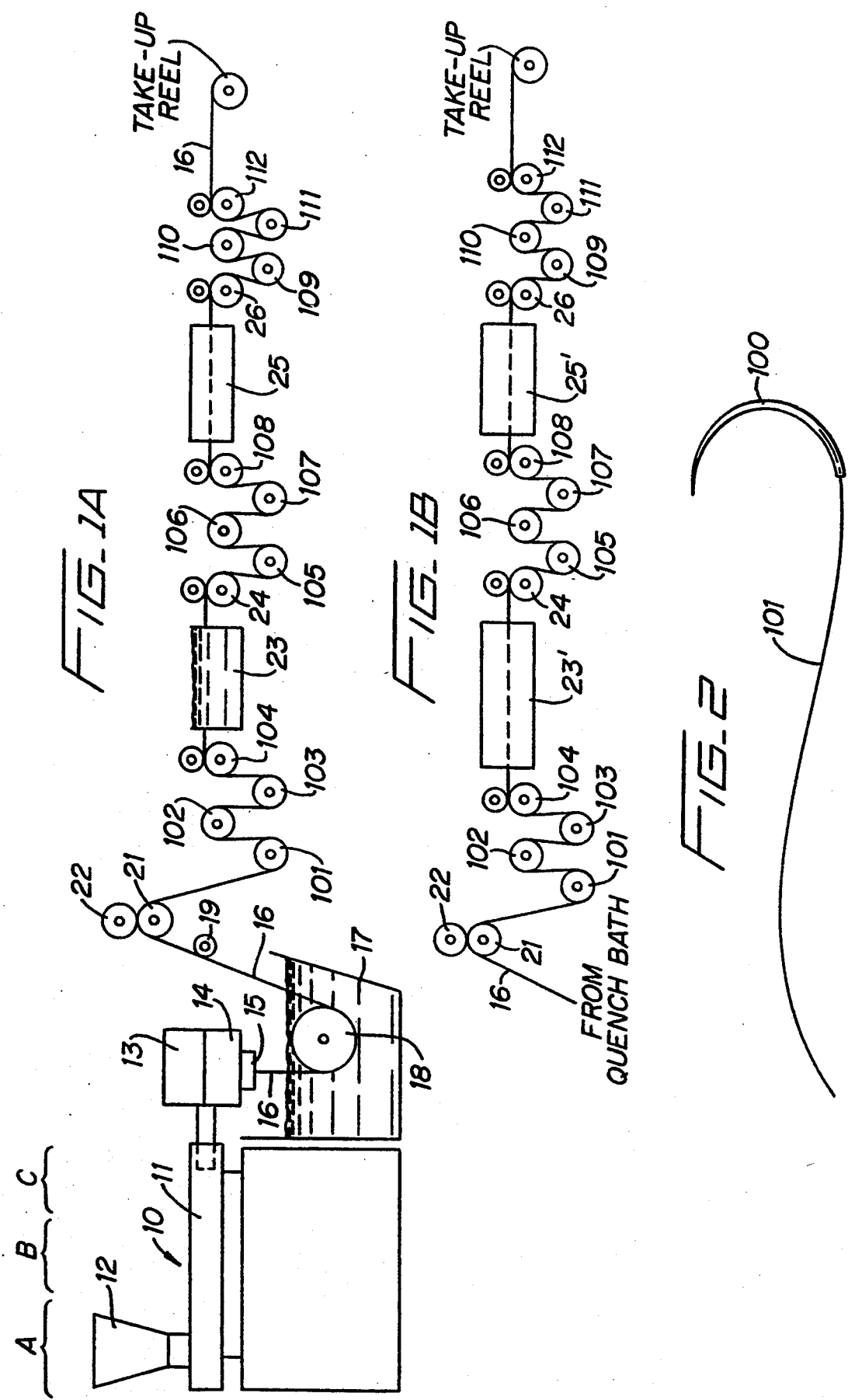

& nbsp;
ABSORBABLE BLOCK COPOLYMERS AND SURGICAL ARTICLES FABRICATED THEREFROM This application is a continuation-in-part of U.S. patent application Ser. No. 08/068,811, filed May 27, 1993) now abandoned.

TECHNICAL FIELD

The present invention relates to absorbable block copolymers having one of the blocks predominantly hard phase forming monomers and another of said blocks made from randomly copolymerized soft phase forming monomers, and more particularly to surgical articles made totally or in part therefrom, including both monofilament and multifilament sutures.

BACKGROUND OF THE INVENTION

Polymers and copolymers of, and surgical devices made from lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo- and copolymers: 1, "*Polymer,* Volume 20, pages 1459–1464 (1979), and D. F. Williams (ed.) *Biocompatibility Of Clinical Implant Materials,* Volume II, chapter 9: "Biodegradable Polymers" (1981).

Surgical devices prepared from copolymers containing lactide or glycolide and trimethylene carbonate have been described.

U.S. Pat. No. 4,429,080 describes glycolide end blocks and glycolide trimethylene carbonate random copolymer middle blocks. The block copolymers described in the '080 patent contain no 1,4 dioxane-2-one.

As another example, U.S. Pat. No. 5,066,772 describes random copolymers of lactide and trimethylene carbonate and triblock copolymers having lactide end blocks and lactide-trimethylene carbonate random copolymer center blocks. The block copolymers of the '772 patent do not include a block which has predominantly glycolic acid ester linkages.

Block copolymers described in U.S. Pat. No. 5,145,945 do not include a block having random copolymers of trimethylene carbonate and dioxanone nor do they include a block which is predominantly glycolide. In addition, see U.S. Pat. Nos. 4,243,775; 4,300,565; 4,705,820; 4,891,263; 4,916,193; 4,902,203; 5,037,950, and 5,252,701.

As described above bioabsorbable sutures are known in the art. However, in the manufacture of sutures an important characteristic of a suture is the amount of effort typically required to straighten the suture upon its removal from the package in order to ready the suture for use. This effort appears to be related to the "strain energy" of the suture, i.e., the integration of the stress-strain curve for the suture measured in kilogram-mm, and is equivalent to the work expended in elongating the monofilament by a specified percentage of its original length. As the strain energy of a given size of suture decreases so, too, does the amount of effort required to straighten the suture prior to use. A decrease in strain energy also appears to relate to the perceived flexibility of the suture, another important characteristic.

Therefore, it would be advantageous to provide a bioabsorbable suture which exhibits good flexibility and handling characteristics while maintaining other desired characteristics, such as knot strength, knot retention and desired absorption characteristics.

SUMMARY OF THE INVENTION

It has now been found that absorbable surgical articles may be formed from a block copolymer having one of the blocks made from hard phase forming monomers and another of the blocks made from random copolymers of soft phase forming monomers. Hard phase forming monomers include glycolide and lactide while soft phase forming monomers include 1,4 dioxane-2-one and 1,3 dioxane-2-one and caprolactone.

Preferably, block copolymers useful in forming surgical articles in accordance with the present invention include block copolymers comprising one block having glycolic acid ester units as a predominant component thereof. A "predominant component" is a component which is present in an amount greater than 50 percent.

In a particularly useful embodiment the block copolymers of the present invention may be spun into fibers. The fibers can be fabricated into both monofilament and braided multifilament sutures.

In another aspect of the present invention there is provided a process for manufacturing a suture exhibiting excellent energy and/or increased knot performance for a given size comprising the operations of extruding the block copolymer of the present invention at an extrusion temperature of from about 170° C. to about 250° C. to provide a monofilament fiber, stretching the solidified monofilament at a temperature of from about 20° C. to about 90° C. in water (or other suitable liquid medium) or at from about 30° C. to about 100° C. in air (or other suitable gaseous medium) at a stretch ratio of from about 3:1 to about 10:1 to provide a stretched monofilament. The stretched monofilament preferably is then frozen at a temperature of from about −15° C. to about 0° C. The suture then may be annealed with or without relaxation at a temperature of from about 80° C. to about 130° C. to provide the finished suture.

BRIEF DESCRIPTION OF THE DRAWINGS

FIG. 1A is a schematic illustration of an apparatus which is suitable for manufacturing the monofilament suture of this invention.

FIG. 1B is a modification of the apparatus of FIG. 1A which is particularly suitable for manufacturing the monofilament sutures of the present invention of smaller size, e.g., sizes 4/0 and smaller.

FIG. 2 is a perspective view of a suture of the present invention attached to a needle.

DESCRIPTION OF THE PREFERRED EMBODIMENTS

In accordance with the present invention, it has been found that a block copolymer having two specific types of blocks, an "A" block having a proportion of glycolic acid ester units as the predominant component thereof and a "B" block comprising 1,3 dioxane-2-one randomly copolymerized with 1,4 dioxane-2-one, can advantageously be combined to form a block copolymer useful in forming surgical elements.

The block copolymer compositions of the present invention include an A block formed from a copolymer which has glycolide as the predominant component thereof. That is, glycolide comprises at least 50 mole percent of the first block. Preferably, glycolide comprises at least about 60 mole percent of the first block and most preferably at least about 95 mole percent glycolide. The glycolide may be copolymerized with any monomer which provides an absorbable copolymer to form the A block. Such monomers include but are not limited to lactide, trimethylene carbonate, p-dioxanone, and epsilon-caprolactone. The copolymers of glycolide which form the first block can be random or block copolymers and can be synthesized by known methods. See, for example. U.S. Pat. Nos. 4,653,497; 4,838,267; 4,429,080; 4,605,730; and 4,788,979 the disclosures of which are incorporated herein by reference.

The B block of the composition of this invention has 1,4 dioxane-2-one and 1,3 dioxane-2-one linkages. Preferably 1,4 dioxane-2-one comprises from about 20 mole percent to about 80 mole percent, and more preferably from about 35 mole percent to about 65 mole percent of the B block. Most preferably, 1,4 dioxane-2-one comprises at least about 35 mole percent of the B block, the remainder of the block comprising 1,3 dioxane-2-one. For purposes of the present invention, copolymers of 1,3 dioxane-2-one and 1,4 dioxane-2-one having an inherent viscosity of from about 0.5 to about 2 dl/g measured at 30° C. and a concentration of 0.25 g/dl in chloroform or HFIP may generally be used as the second block.

The block copolymers of this invention may be prepared by preparing the individual polymers which make up the blocks and then copolymerizing these polymers to form a block or graft copolymer. Alternatively, a pre-polymer having 1,4 dioxane-2-one and 1,3 dioxane-2-one linkages may be prepared in a reactor and then the monomers needed to form the other block or blocks are added directly to the reactor to thereby form the block copolymer. In one embodiment the polymerization reaction used in the formation of the above mentioned pre-polymer is stopped short of completion, leaving residual 1,4 dioxane-2-one. Then monomers needed to form the other block or blocks are added directly to the reactor vessel to react with the residual 1,4 dioxane-2-one and the pre-polymer to form block copolymers having 1,4 dioxane-2-one linkages in each block.

In forming the block copolymers of this invention, the A (predominantly glycolide) block may be present in an amount from about 50 to about 80 percent by weight based on the weight of the final block copolymer. The B (random copolymer) block may be present in an amount from about 20 to about 50 weight percent based on the weight of the final block copolymer, Preferably, the A block comprises between about 60 and about 70 weight percent of the block copolymer. In a particularly useful embodiment, the A block comprises about 70 weight percent and the B block comprises about 30 weight percent of the final block copolymer. The copolymers of the present invention have a molecular weight such that their inherent viscosity is from about 0.8 to about 1.6 dl/g, and preferably from about 1 to about 1.40 dl/g measured at 30° C. at a concentration of 0.25 g/dl in chloroform or hexafluoroisopropanol (HFIP).

Each A and B block may comprise a single type of recurring monomeric unit. Alternatively, each block may comprise more than one type of recurring monomeric unit randomly distributed throughout each block. The block copolymers of the present invention may have repeating block units such as AB, ABA, ABAB, ABABA, BABA, etc.; with ABA being preferred.

The block copolymers of thins invention can be formed into surgical articles using any know technique, such as, for example, extrusion, molding and/or solvent casting. The copolymers can be used alone, blended with other absorbable compositions, or in combination with non-absorbable components. A wide variety of surgical articles can be manufactured from the copolymer of the present invention. These include but are not limited to clips and other fasteners, staples, sutures, pins, screws, prosthetic devices, wound dressings, drug delivery devices, anastomosis rings, and other implantable devices. Fibers made from the copolymers of this invention can be knitted or woven with other fibers, either absorbable or nonabsorbable to form meshes or fabrics. The compositions of this invention can also be used as an absorbable coating for surgical devices. Preferably, however, the copolymers are spun into fibers to be used as Sutures, either monofilament or multifilament.

Multifilament sutures of the present invention may be made by methods known in the art. Braid constructions such as those disclosed and claimed in U.S. Pat. Nos. 5,059,213 and 5,019,093 are suitable for the multifilament suture of the present invention.

A suitable process for the manufacture of monofilament sutures of the present invention comprises the operations of melt extruding the resin at an extrusion temperature of from about 170° C. to about 250° C. to provide a monofilament, stretching the solidified monofilament at a temperature of from about 20° C. to about 90° C. in water (or other suitable liquid medium) or at from about 30° C. to about 100° C. in air (or other suitable gaseous medium) at a stretch ratio of from about 3:1 to about 10:1 to provide a stretched monofilament. Optionally, the solidified monofilament may be stretched in air or other suitable gaseous medium preferably at about 100° C. Preferably, the monofilament is then frozen at a temperature of from about −15° C. to about 0°C. The suture may then be annealed at a temperature of from about 50° C. to about 130° C. to provide the finished suture.

FIG. 1A schematically illustrates a monofilament suture manufacturing operation which is especially suitable for producing larger size sutures, e.g., those of sizes 3/0 and larger. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of resins of the present invention are introduced to the extruder through hopper 12. Any of the block copolymers of the present invention which are useful for the formation of fibers can be used herein.

Motor-driven metering pump 13 delivers melt extruded resin at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact with air currents which might otherwise effect the cooling of the monofilament in an unpredictable manner. In general, barrel zone A of the extruder can be maintained at a temperature of from about 170° C. to 220° C., zone B at from about 180° C. to 230° C. and zone C at from about 190° C. to about 240° C. Additional temperature parameters include: metering pump block 13 at from about 180° C. to about 230° C., spin pack 14 at from about 190° C. to about 230° C., spinneret 15 at from about 180° C. to about 230° C. and quench bath at from about 10° C. to about 80° C.

Monofilament 16 is passed through quench bath 17 around driven roller 18 and over idle roller 19. Optionally, a wiper (not shown) may remove excess water from the monofilament as it is removed from quench bath 17. On exiting the quench bath the monofilament is wrapped around a first godet 21 provided with nip roll 22 to prevent slippage which might otherwise result from the subsequent stretching operation; and subsequently wrapped around godets 101, 102, 103 and 104 or any other suitable godet arrangement. Monofilament 16 passing from godet 104 is stretched, e.g., With stretch ratios on the order of from about 3:1 to about 10:1 and preferably from about 4:1to about 7:1, to effect its orientation and thereby increase its tensile strength.

In the stretching operation shown in FIG. 1A, generally suitable for larger size sutures, e.g., sizes 2 to 3/0, monofilament 16 is drawn through hot water (or other suitable liquid medium) draw bath 23 by means of godets 24, 105, 106, 107 and 108 or any other suitable arrangement of godets which rotate at a higher speed than godet 104 to provide the desired stretch ratio. The temperature of hot water draw bath 23 is advantageously from about 30° C. to about 90° C. and preferably is from about 30° C. to about 50° C.

In the alternative stretching operation shown in FIG. 1B, generally preferred for smaller sutures sizes, e.g., sizes 4/0 to 8/0, monofilament 16 is drawn by godets 24, 105, 106, 107, and 108 or any other suitable godet arrangement through hot air convection oven chamber 23' at a temperature of from about 30° C. to about 80° C. and preferably from about 30° C. to about 60° C. to provide the desired
 amount of stretch. Following the stretching operation shown in FIG. 1A or 1B, monofilament 16 optionally may be subjected to an on-line annealing and/or additional stretching without shrinkage or relaxation with shrinkage operation as a result of which the monofilament shrinks. In the processes of FIGS. 1A and 1B, on line annealing with or without relaxation when desired is accomplished by driving monofilament 16 by godets 26, 109, 110, 111, and 112 or any other suitable godet arrangement through second hot air oven chamber 25 at a temperature of from about 30° C. to about 120° C. and preferably from about 30° C. to about 60° C. During the relaxation process, at these temperatures, monofilament 16 will generally recover to within about 80 to about 97 percent, and preferably to within about 95 percent, of its pre-annealed length to provide the finished s For relaxation, the third godet rotates at a slower speed than the second godet thus relieving tension on the filament.

Annealing of the suture also may be accomplished without shrinkage of the suture. In carrying out the annealing operation, the desired length of suture may be wound around a creel and the creel placed in a heating cabinet maintained at the desired temperature, e.g. about 70° C. to about 150° C., as described in U.S. Pat. No. 3,630,205. After a suitable period of residency in the heating cabinet, e.g., about 18 hours or so, the suture will have undergone essentially no shrinkage. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The suture of the present invention, suture 101, may be attached to a surgical needle 100 as shown in FIG. 2 by methods well known in the art. Wounds may be sutured by passing the needled suture through tissue to create wound closure. The needle preferably is then removed from the suture and the suture tied.

It is further within the scope of this invention to incorporate one or more medico-surgically useful substances into the present invention, e.g., those which accelerate or beneficially modify the healing process when particles are applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It is contemplated that it may be desirable to dye the sutures of the present invention in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, sutures in accordance with the invention are dyed by adding up to about a few percent and preferably about 0.2% dye, such as D&C Violet No. 2 to the resin prior to extrusion.

In order that those skilled in the art may be better able to practice the present invention, the following examples are given as an illustration of the preparation Of block copolymer of the present invention as well as of the preparation and superior characteristics of the sutures of the present invention. It should be noted that the invention is not limited to the specific details embodied in the examples and further that all ratios or parts recited are by weight.

EXAMPLE 1

1,3 dioxane-2-one (1137.5 grams) and 1,4 dioxan-2-one (741 grams) are added to a reactor along with 0.5 g chloride and 1 gram of diethylene glycol. The mixture is heated and placed at 150° C., with stirring under a nitrogen atmosphere for 3.5 hours. The setting of the reactor is then decreased to 130° and stirring is continued for 3 hours. The 1,3 dioxane-2-one/1,4 dioxane-2-one copolymer is then sampled.

Five hundred grams of dry glycolide are then added to the reactor. The setting for the temperature of the reactor is then increased to 210° C. When the temperature of the reactor reaches 195° C., 2750 grams of glycolide are added with continued stirring. The polymerization is continued for about 45 minutes.

The reaction product is isolated, comminuted, and treated to remove residual reactants using known techniques.

EXAMPLE 2

1,3 dioxane-2-one (1300 gram) and 1,4 dioxane-2-one (840 grams) are added to a reactor along with 0.5 of stannous chloride and 1 gram of diethylene glycol. The mixture is heated and placed at 150° C. (with stirring) under a nitrogen atmosphere for 3.5 hours. The setting of the reactor is then decreased to 130° C. and stirring is continued for 3 hours. The 1,3 dioxane-2-one/1,4 dioxane-2-one copolymer is then sampled.

Five hundred grams of dry glycolide are then added to the reactor. The setting for the temperature of the reactor is then increased to 210° C. When the temperature of the reactor reaches 195° C., 2500 grams of glycolide are added with continued stirring. The polymerization is continued for about forty five minutes.

The reaction product is isolated comminuted, and treated to remove residual reactants using known techniques. The copolymer is then heated under vacuum to. remove residual water, residual solvent and/or unreacted monomer.

Table I below sets forth typical conditions for extruding, stretching various sizes of sutures in accordance with this invention. All of the monofilament sutures were fabricated from the resin of Example 1 and Example 2.

TABLE I

CONDITIONS OF MANUFACTURING MONOFILAMENT SUTURES OF THE PRESENT INVENTION

| Example | 1 | 2 |
|---|---|---|
| Suture Size | 3/0 | 3/0 |
| Process Conditions | Extrusion | Operation |
| extruder screw, rpm | 3.1 | 1.6 |
| pump, rpm | 12.6 | 6.1 |
| barrel temp., °C., zone A | 195 | 190 |
| barrel temp., °C., zone B | 200 | 196 |
| barrel temp., °C., zone C | 208 | 200 |
| clamp temp., °C., | 208 | 200 |
| adapter temp., °C. | 208 | 200 |
| pump temp., °C. | 209 | 195 |

TABLE I-continued

CONDITIONS OF MANUFACTURING MONOFILAMENT SUTURES OF THE PRESENT INVENTION

| Example | 1 | 2 |
|---|---|---|
| block temp., °C. | 209 | 195 |
| barrel melt temp., °C. | 201 | 208 |
| pump melt temp., °C. | 202 | 198 |
| spinneret melt temp., °C. | 202 | 201 |
| barrel pressure, psi | 1400 | 1758 |
| pump pressure, psi | 1400 | 1791 |
| spinneret pressure, psi | 900 | 882 |
| pump size, cc per revolution | 0.16 | 0.297 |
| diameter of spinneret, orifices, mm | 1.25 | 1.25 |
| no. of spinneret orifices | 1 | 1 |
| quench bath temp., °C. | 17 | 20 |
| Stretching (orienting) operation | | |
| draw bath temp., °C. | 32 | 32 |
| first godet, mpm | 4.6 | 5.3 |
| second godet, mpm | 3 | 29.4 |
| second oven temp, °C. | 33 | 33 |
| third godet, mpm | 30 | 29.3 |
| draw ratio | 6.5:1 | 5.5:1 |
| Freezing Operation | | |
| temp., °C. | −13 | −13 |
| time (hrs.) | 18 | 18 |
| Annealing Operation | | |
| oven temp., °C. | 105 | 70 |
| time (hrs.) | 18 | 18 |

The physical properties of the sutures and the procedures employed for their measurement are set forth in Table II as follows:

TABLE II

PROCEDURES FOR MEASURING PHYSICAL PROPERTIES OF MONOFILAMENT SUTURES OF THE PRESENT INVENTION

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ASTM D-2256 |
| tensile strength, kg/mm² | ASTM D-2256, Instron Corporation Series IX Automated Materials Testing System 1.03A |
| 0–5% and 0–10% strain energies, kg-mm | ASTM D-2256, Instron Corporation Series IX Automated Materials Testing System 1.03A |

Table III below sets forth the physical properties of the size 3/0 suture of the present invention.

TABLE III

| Physical Property | Example 1 | Example 2 |
|---|---|---|
| diameter (mm) | 0.3 | 0.29 |
| knot-pull strength (kg) | 2.9 | 2.4 |
| Young's Modulus (kpsi) | 190 | 145 |
| Straight-pull strength (kg) | 4.4 | 3.7 |
| Strain Energy 0–5% (kg-mm) | 1.28 | 0.84 |
| Strain Energy 0–10% (kg-mm) | 3.89 | 2.76 |
| Elongation (%) | 47 | 44 |
| Tensile Strength (kg/mm²) | 60.6 | 55.3 |

Comparative Example

TABLE IV Below sets forth the physical properties of a size 3/0 Maxon suture, which is made from a glycolide/glycolide-co-trimetlylene carbonate/glycolide copolymer (commercially available from Davis & Geck, Danbury, Conn.)

TABLE IV

| diameter (mm) | 0.293 |

TABLE IV-continued

| | |
|---|---|
| Knot-pull strength (kg) | 2.9 |
| Young's Modulus (kpsi) | 425 |
| Straight-pull strength (kg) | 3.9 |
| Strain Energy 0–5% (kg-mm) | 1.6 |
| Strain Energy 0–10% (kg-mm) | 5.19 |
| Elongation (%) | 30 |
| Tensile Strength (kg/mm$^2$) | 56.2 |

As the data in Tables III and IV illustrate, the suture made of the copolymer of the present invention showed improved flexibility while demonstrating acceptable physical properties, such as knot pull and straight-pull strength.

EXAMPLE 3

Monofilament sutures manufactured in accordance with the above described process using the copolymer of Example 2 were tested for straight-pull strength, knot-pull strength, Young's Modulus and in vitro strength retention. Straight-pull strength and knot-pull strength were tested in accordance with the test procedures described in Table II hereinabove. Young's Modulus, a measurement of flexibility, is the initial modulus as determined from the slope of stress-strain curves produced in the straight-pull tests. Young's Modulus is the ratio of applied stress to strain in the elastic region (initial linear portion of curves).

The in vitro strength retention of the suture was tested as follows:

To simulate in vivo conditions, the suture samples were stored in a container filled with Sorenson's buffer solution at 37° C. After various periods of time, the suture samples were then removed from the container to test their knot-pull strength, using an Instron tensile tester. In vitro knot-pull strength retention is indicative of in vivo strength retention.

The results of the tests are presented in Table IV hereinbelow. In the strength retention data reported in Table IV, $T_n$ represents the time elapsed in weeks since the sample was placed in the solution, with n representing the number of weeks. Straight-pull strength, knot-pull strength and Modulus measurements were taken at time T0. For comparison purposes, the same tests were conducted on a Maxon suture, which is made from a glycolide/glycolide-trimethylene carbonate/glycolide copolymer (commercially available in 1993 from Davis and Geck, Danbury, Conn.); PDSII suture, which is made from polydioxanone homopolymer (commercially available from Ethicon, Inc., Summerville, N.J.); Monocryl suture, which is made from a glycolide/glycolide-caprolactone/glycolide copolymer (commercially available from Ethicon, Inc., Summerville, N.J.). All comparative tests were performed on size 3/0 sutures.

Monocryl, while showing acceptable knot-pull and straight-pull strengths. The suture of Example 2 further exhibits an in vitro strength retention greater than Monocryl and less than Maxon and PDSII.

Obviously, other modifications and variations of the present invention are possible in light of the above teachings. It is therefore to be understood that changes may be made in particular embodiments of the invention described which are within the full intended scope of the invention as defined by the claims.

What is claimed is:

1. A block copolymer comprising:
   a) a proportion of glycolic acid ester units as one of said blocks, and
   b) another of said blocks comprising 1,4 dioxan-2-one randomly polymerized with 1,3 dioxane-2-one.

2. The block copolymer of claim 1, wherein glycolic acid ester units comprise from about 50 to about 80 percent by weight of said block copolymer.

3. The block copolymer of claim 1, wherein said blocks comprising random copolymers of 1,4 dioxan-2-one and 1,3 dioxane-2-one comprise from about 20 to about 50 percent by weight of said block copolymer.

4. The block copolymer of claim 3, wherein said blocks comprising random copolymers of 1,4 dioxan-2-one and 1,3 dioxane-2-one are formed from the random polymerization of about 35 percent by weight of 1,4 dioxan-2-one and about 65 percent by weight 1,3 dioxane-2-one.

5. The block copolymer of claim 1, wherein component (a) comprises a predominant amount of glycolic acid ester units, the remainder being 1,4 dioxane-2-one.

6. The block copolymer of claim 5 wherein component (b) consists essentially of 1,4 dioxane-2-one randomly polymerized with 1,3 dioxane-2-one.

7. The block copolymer of claim 1, wherein said block copolymer is a tri-block copolymer.

8. The tri-block copolymer of claim 7, comprising:
   a) a proportion of glycolic acid ester units as end blocks, and
   b) a center block comprising 1,4 dioxan-2-one randomly polymerized with 1,3 dioxane-2-one.

9. The tri-block copolymer of claim 8, wherein said end blocks comprise from about 50 to about 80 percent by weight of said tri-block copolymer.

10. The tri-block copolymer of claim 8, wherein said end blocks comprise a predominant amount of glycolic acid ester units, the remainder being 1,4 dioxane-2-one.

11. The tri-block copolymer of claim 10, wherein said center block consists essentially of 1,4 dioxane-2-one randomly polymerized with 1,3 dioxane-2-one.

12. The tri-block copolymer of claim 9, wherein said center block is formed from the random polymerization of about 35 percent of 1,4 dioxan-2-one and about 65 percent of 1,3 dioxane-2-one, by weight of said center block.

TABLE V

| COMPOSITION wt % | KNOT kpsi | STRAIGHT kpsi | MODULUS kpsi | IN VITRO STRENGTH RETENTION | | | | | | | |
|---|---|---|---|---|---|---|---|---|---|---|---|
| | | | | $T_1$ % | $T_2$ % | $T_3$ % | $T_4$ % | $T_6$ % | $T_8$ % | $T_{10}$ % | $T_{12}$ % |
| MAXON | 61 | 82 | 425 | 88 | 81 | 70 | 69 | 33 | — | — | — |
| MONOCRYL | 51 | 97 | 105 | 51 | 21 | 3 | — | — | — | — | — |
| PDSII | 48 | 77 | 210 | — | — | — | 84 | — | 34 | — | 10 |
| VICRYL | 36 | 88 | 844 | 91 | 64 | 35 | — | — | — | — | — |
| EXAMPLE 2 | 50 | 80 | 145 | 82 | 66 | 37 | 8 | — | — | — | — |

As the data in Table V demonstrates, the suture made of a copolymer of the present invention demonstrated a modulus lower than Maxon and PDSII, comparable to block.

13. A surgical article formed totally or in part from the block copolymer of claim 1.

14. The surgical article of claim 13, wherein said surgical article is selected from the group consisting of clips, staples, sutures, pins, screws, prosthetic devices, anastomosis rings and growth matrices.

15. The surgical article of claim 14, wherein said suture is a monofilament suture.

16. A method of making a copolymer comprising the steps of:
   a) adding 1,4 dioxane-2-one and 1,3 dioxane-2-one;
   b) polymerizing component (a) to the point where all the 1,3 dioxane-2-one is incorporated in a polymer but residual 1,4 dioxane-2-one monomer remains;
   c) adding glycolide; and
   d) polymerizing.

17. The method of claim 16, further comprising the step of removing residual monomer.

* * * * *